(12) United States Patent
Patel et al.

(10) Patent No.: US 11,207,489 B2
(45) Date of Patent: Dec. 28, 2021

(54) ENHANCED BRAIN-MACHINE INTERFACES WITH NEUROMODULATION

(71) Applicant: HRL Laboratories, LLC, Malibu, CA (US)

(72) Inventors: Aashish N. Patel, Cordova, TN (US); Praveen K. Pilly, West Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 323 days.

(21) Appl. No.: 16/426,198

(22) Filed: May 30, 2019

(65) Prior Publication Data

US 2019/0314600 A1    Oct. 17, 2019

Related U.S. Application Data

(63) Continuation-in-part of application No. 15/332,787, filed on Oct. 24, 2016, now Pat. No. 10,307,592.

(Continued)

(51) Int. Cl.
*A61M 21/00*   (2006.01)
*A61F 2/72*    (2006.01)
(Continued)

(52) U.S. Cl.
CPC .............. *A61M 21/00* (2013.01); *A61B 5/291* (2021.01); *A61F 2/72* (2013.01); *A61M 2021/0027* (2013.01); *A61M 2021/0044* (2013.01); *A61M 2021/0055* (2013.01); *A61M 2205/3313* (2013.01); *A61M 2205/502* (2013.01); *A61M 2205/52* (2013.01); *A61M 2230/10* (2013.01); *A61N 1/0456* (2013.01)

(58) Field of Classification Search
CPC .... A61N 1/36025; A61N 1/20; A61B 5/0476; A61B 5/4836; A61B 5/4812
See application file for complete search history.

(56) References Cited

U.S. PATENT DOCUMENTS

2005/0228515 A1    10/2005    Musallam et al.
2011/0092882 A1    4/2011    Firlik et al.
(Continued)

OTHER PUBLICATIONS

Astaras, Alexander, et al. "Towards brain-computer interface control of a 6-degree-of-freedom robotic arm using dry EEG electrodes." Advances in Human-Computer Interaction 2013 (2013): 2, pp. 1-7.

(Continued)

*Primary Examiner* — Rex R Holmes
(74) *Attorney, Agent, or Firm* — Tope-McKay & Associates (57) ABSTRACT

Described is an improved brain-machine interface including a neural interface and a controllable device in communication with the neural interface. The neural interface includes a neural device with one or more sensors for collecting signals of interest and one or more processors for conditioning the signals of interest, extracting salient neural features from and decoding the conditioned signals of interest, and generating a control command for the controllable device. The controllable device performs one or more operations according to the control command, and the neural device administers neuromodulation stimulation to reinforce operation of the controllable device.

15 Claims, 4 Drawing Sheets

Related U.S. Application Data (60) Provisional application No. 62/245,730, filed on Oct. 23, 2015, provisional application No. 62/712,447, filed on Jul. 31, 2018.

(51) Int. Cl.
*A61B 5/291* (2021.01)
*A61N 1/04* (2006.01)

(56) References Cited

U.S. PATENT DOCUMENTS

| 2011/0307079 | A1* | 12/2011 | Oweiss | A61B 5/4094 623/27 |
|---|---|---|---|---|
| 2016/0228705 | A1 | 8/2016 | Crowder et al. | |
| 2017/0028197 | A1 | 2/2017 | Wingeier et al. | |
| 2018/0168905 | A1 | 6/2018 | Goodall et al. | |

OTHER PUBLICATIONS

Mankin, Emily A., et al. "Hippocampal CA2 activity patterns change over time to a larger extent than between spatial contexts." Neuron 85.1 (2015): pp. 190-201.
Chi, Zhiyi, and Daniel Margoliash. "Temporal precision and temporal drift in brain and behavior of zebra finch song." Neuron 32.5 (2001): pp. 899-910.
Wheeler, Kevin R., and Charles C. Jorgensen. "Gestures as input: Neuroelectric joysticks and keyboards." IEEE pervasive computing 2.2 (2003): pp. 56-61.
Bashivan, Pouya, et al. "Learning representations from EEG with deep recurrent-convolutional neural networks." arXiv preprint arXiv:1511.06448 (2015), pp. 1-15.
Elango, Venkatesh, et al. "Sequence Transfer Learning for Neural Decoding." bioRxiv (2017): 210732, pp. 1-11.
Pan, Lizhi, et al. "Transcranial direct current stimulation versus user training on improving online myoelectric control for amputees." J. Neural Eng 14.046019 (2017): 046019, pp. 1-15.
Patel, Aashish, et al. "Mental state assessment and validation using personalized physiological biometrics." Front. Hum. Neurosci. 2018. vol. 12, Article 221, pp. 1-13.
Marshall L, Helgadóttir H, Mölle M, Born J. Boosting slow oscillations during sleep potentiates memory. Nature. 2006 444(7119): pp. 610-613.
Rudoy JD, Voss JL, Westerberg CE, Paller KA. Strengthening Individual Memories by Reactivating Them During Sleep. Science. Nov. 20, 2009;326(5956): pp. 1079-1079.
Diekelmann S, Biggel S, Rasch B, Born J. Offline consolidation of memory varies with time in slow wave sleep and can be accelerated by cuing memory reactivations. Neurobiol Learn Mem. Sep. 2012; 98(2): pp. 103-111.
Rasch BH, Born J, Gais S. Combined blockade of cholinergic receptors shifts the brain from stimulus encoding to memory consolidation. J Cogn Neurosci. May 2006; 18(5): pp. 793-802.
Gais S, Born J. Low acetylcholine during slow-wave sleep is critical for declarative memory consolidation. Proc Natl Acad Sci U S A. Feb. 17, 2004; 101(7): pp. 2140-2144.
Rasch B, Buchel C, Gais S, Born J. Odor cues during slow-wave sleep prompt declarative memory consolidation. Science. 2007; 315(5817): pp. 1426-1429.
Kirov R, Weiss C, Siebner HR, Born J, Marshall L. Slow oscillation electrical brain stimulation during waking promotes EEG theta activity and memory encoding. Proc. Natl. Acad. Sci. 2009;106: pp. 15460-15465.
Jutras MJ, Fries P, Buffalo EA. Oscillatory activity in the monkey hippocampus during visual exploration and memory formation. Proc Natl Acad Sci. Aug. 6, 2013; 110(32): pp. 13144-13149.
Brincat SL, Miller EK. Frequency-specific hippocampal-prefrontal interactions during associative learning. Nat Neurosci. Apr. 2015; 18(4): pp. 576-581.
McNamara CG, Tejero-Cantero A, Trouche S, Campo-Urriza N, Dupret D. Dopaminergic neurons promote hippocampal reactivation and spatial memory persistence. Nat Neurosci. 2014 12//print; 17(12): pp. 1658-1660.
Ji D, Wilson MA. Coordinated memory replay in the visual cortex and hippocampus during sleep. Nat Neurosci. 2007; 10(1): pp. 100-107.
Kali S, Dayan P. Off-line replay maintains declarative memories in a model of hippocampal-neocortical interactions. Nat Neurosci. 2004; 7(3): pp. 286-294.
Rolls ET. Hippocampo-cortical and cortico-cortical backprojections. Hippocampus. 2000; 10: pp. 380-388.
Creutzfeldt OD, Fromm GH, Kapp H. Influence of transcortical d-c currents on cortical neuronal activity. Exp Neurol. Jun. 1962; 5: p. 436-452.
Sederberg PB, Kahana MJ, Howard MW, Donner EJ, Madsen JR. Theta and gamma oscillations during encoding predict subsequent recall. J Neurosci Off J Soc Neurosci. Nov. 26, 2003; 23(34): pp. 10809-10814.
Osipova D, Takashima A, Oostenveld R, Fernandez G, Maris E, Jensen O. Theta and gamma oscillations predict encoding and retrieval of declarative memory. J Neurosci. 2006; 26(28): pp. 7523-7531.
Fröhlich F, McCormick DA. Endogenous electric fields may guide neocortical network activity. Neuron. Jul. 15, 2010; 67(1): pp. 129-143.
Ngo, H. V. V., Martinetz, T., Born, J., & Mölle, M. (2013). Auditory closed-loop stimulation of the sleep slow oscillation enhances memory. Neuron, 78(3), pp. 545-553.
Office Action 1 for U.S. Appl. No. 15/332,787, dated Sep. 18, 2018.
Response to Office Action 1 for U.S. Appl. No. 15/332,787, dated Nov. 6, 2018.
Notice of Allowance for U.S. Appl. No. 15/332,787, dated Jan. 17, 2019.
Notification of the International Preliminary Report on Patentability Chapter I for PCT/US2019/034516; dated Feb. 11, 2021.
The International Preliminary Report on Patentability Chapter I for PCT/US2019/034516; dated Feb. 11, 2021.
Notification of Transmittal of International Search Report and the Written Opinion of the International Searching Authority for PCT/US2019/034516; dated Sep. 23, 2019.
International Search Report of the International Searching Authority for PCT/US2019/034516; dated Sep. 23, 2019.
Written Opinion of the International Searching Authority for PCT/US2019/034516; dated Sep. 23, 2019.

\* cited by examiner

ENHANCED BRAIN-MACHINE INTERFACES WITH NEUROMODULATION

CROSS-REFERENCE TO RELATED APPLICATIONS

This is a Continuation-in-Part Application of U.S. application Ser. No. 15/332,787, issued as U.S. Pat. No. 10,307,592 on Jun. 4, 2019, filed in the United States on Oct. 24, 2016, entitled, "Method and System to Accelerate Consolidation of Specific Memories Using Transcranial Stimulation," which is a Non-Provisional patent application of 62/245,730, filed in the United States on Oct. 23, 2015, entitled, "Method and System to Accelerate Consolidation of Specific Memories Using Transcranial Stimulation," the entirety of which are hereby incorporated by reference.

This is ALSO a Non-Provisional Application of U.S. Provisional Application No. 62/712,447, filed in the United States on Jul. 31, 2018, entitled, "Enhanced Brain-Machine Interfaces with Neuromodulation," the entirety of which is incorporated herein by reference.

GOVERNMENT LICENSE RIGHTS

This invention was made with government support under U.S. Government Contract Number W911NF-16-C-0018. The government has certain rights in the invention.

BACKGROUND OF INVENTION

(1) Field of Invention

The present invention relates to an enhanced brain-machine interface, and more particularly, to an enhanced brain-machine interface that uses neuromodulation.

(2) Description of Related Art

A brain-machine interface is a direct communication pathway between an enhanced or wired brain and an external device. A brain-machine interface can be used for researching, mapping, assisting, augmenting, or repairing human cognitive or sensory-motor functions.

There is a lack of prior art directly addressing the enhancement of neural interfaces through the utilization of transcranial stimulation, intracranial stimulation, or other neuromodulatory signals. The closest existing prior art that addresses the enhancement of neural control was performed by Pan et al. (see Literature Reference No. 7 in the List of Incorporated Literature References) and focused on using transcranial direct current stimulation to improve the electromyographic response at the periphery.

Coleman (U.S. Publication No. 2015/0351655, which is hereby incorporated by reference as though fully set forth herein) described the direct measurement of neural activity using electroencephalogram (EEG) and manipulation of the neural state by providing direct visual or auditory feedback. This technique is severely limited in its ability to discriminate between different neural processes, or produce a rich set of control outputs. Beyond neuromodulation, other techniques for improving brain-machine interfaces have focused on the improvement of sensor readings and improving decoding techniques.

All prior approaches that utilize neuromodulation focus on utilizing it for improvement of cognitive tasks or physical therapy. The primary reason for this is the limited amount of research in the field. Other prior approaches to improving brain-machine interfaces have been sensor and decoder-centric. However, in addressing accuracy of the neural interface, more advanced decoders that perform well over an extended duration without retraining or recalibration to the subject require a significant amount of data.

Thus, a continuing need exists for a brain-machine interface that utilizes stimulation to improve the neurophysiological response in the brain, not the periphery, and then utilizes that signal to directly control a machine.

SUMMARY OF INVENTION

The present invention relates to an enhanced brain-machine interface, and more particularly, to an enhanced brain-machine interface that uses neuromodulation. The enhanced brain-machine interface comprises a neural interface and a controllable device in communication with the neural interface. The neural interface comprises a neural device having one or more sensors for collecting signals of interest, wherein the neural device is configured to administer neuromodulation stimulation, and one or more processors and a non-transitory computer-readable medium having executable instructions encoded thereon such that when executed, the one or more processors perform operations of conditioning the signals of interest, resulting in conditioned signals of interest; extracting salient neural features from the conditioned signals of interest; decoding the salient neural features, providing a mapping between an input neural feature space and an output control space for the controllable device; based on the mapping, generating at least one control command for the controllable device; causing the controllable device to perform one or more operations according to the at least one control command; and causing the neural device to administer neuromodulation stimulation to reinforce operation of the controllable device.

In another aspect, the signals of interest comprise at least one of neural signals and environmental signals.

In another aspect, the neuromodulation stimulation is one of auditory, visual, and electrical stimulation.

In another aspect, the neuromodulation stimulation comprises unique spatiotemporal amplitude-modulated patterns (STAMPs) of stimulation.

In another aspect, the controllable device is a prosthetic limb.

In another aspect, the one or more neural sensors comprises one or more electrodes configured to perform at least one of sensing and applying stimulation.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to an improved brain-machine interface, and more particularly, to an improved brain-machine interface that uses neuromodulation. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Finally, specific details of various embodiment of the present invention are provided to give an understanding of the specific aspects.

(1) LIST OF INCORPORATED LITERATURE REFERENCES

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number, as follows:

1. Astaras, Alexander, et al. "Towards brain-computer interface control of a 6-degree-of-freedom robotic arm using dry EEG electrodes." Advances in Human-Computer Interaction 2013 (2013): 2.
2. Mankin, Emily A., et al. "Hippocampal CA2 activity patterns change over time to a larger extent than between spatial contexts." Neuron 85.1 (2015): 190-201.
3. Chi, Zhiyi, and Daniel Margoliash. "Temporal precision and temporal drift in brain and behavior of zebra finch song." Neuron 32.5 (2001): 899-910.
4. Wheeler, Kevin R., and Charles C. Jorgensen. "Gestures as input: Neuroelectric joysticks and keyboards." IEEE pervasive computing 2.2 (2003): 56-61.
5. Bashivan, Pouya, et al. "Learning representations from EEG with deep recurrent-convolutional neural networks." arXiv preprint arXiv:1511.06448 (2015).
6. Elango, Venkatesh, et al. "Sequence Transfer Learning for Neural Decoding." bioRxiv (2017): 210732.
7. Pan, Lizhi, et al, "Transcranial direct current stimulation versus user training on improving online myoelectric control for amputees." J. Neural Eng 14.046019 (2017): 046019.
8. Patel, Aashish, et al. "Mental state assessment and validation using personalized physiological biometrics." Front. Hum. Neurosci. 2018. Vol. 12, Article 221.

(2) PRINCIPAL ASPECTS

Various embodiments of the invention include three "principal" aspects. The first is a system for an improved brain-machine interface. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 1:
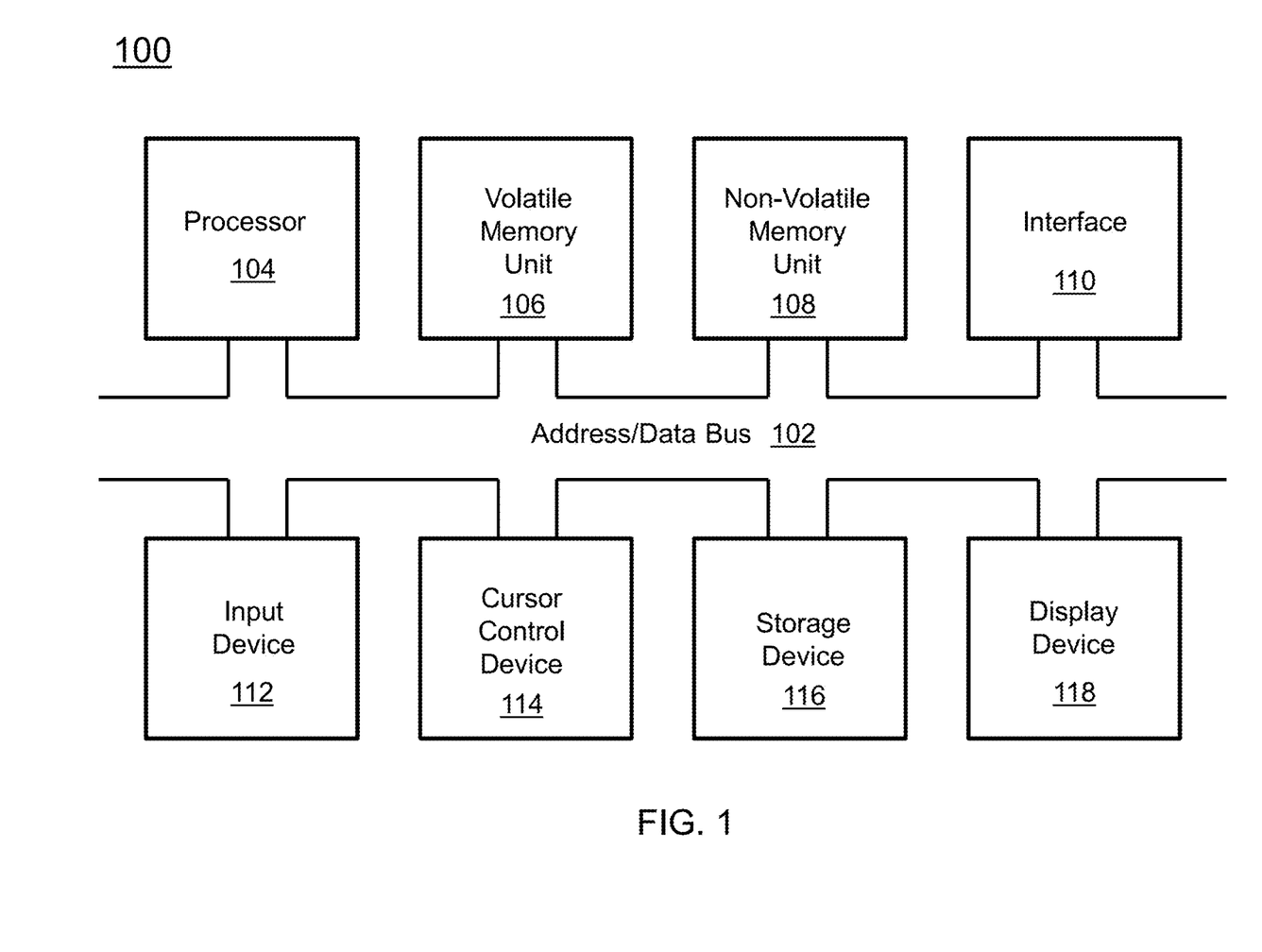
FIG. 1 is a block diagram depicting the components of an improved brain-machine interface according to some embodiments of the present disclosure.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
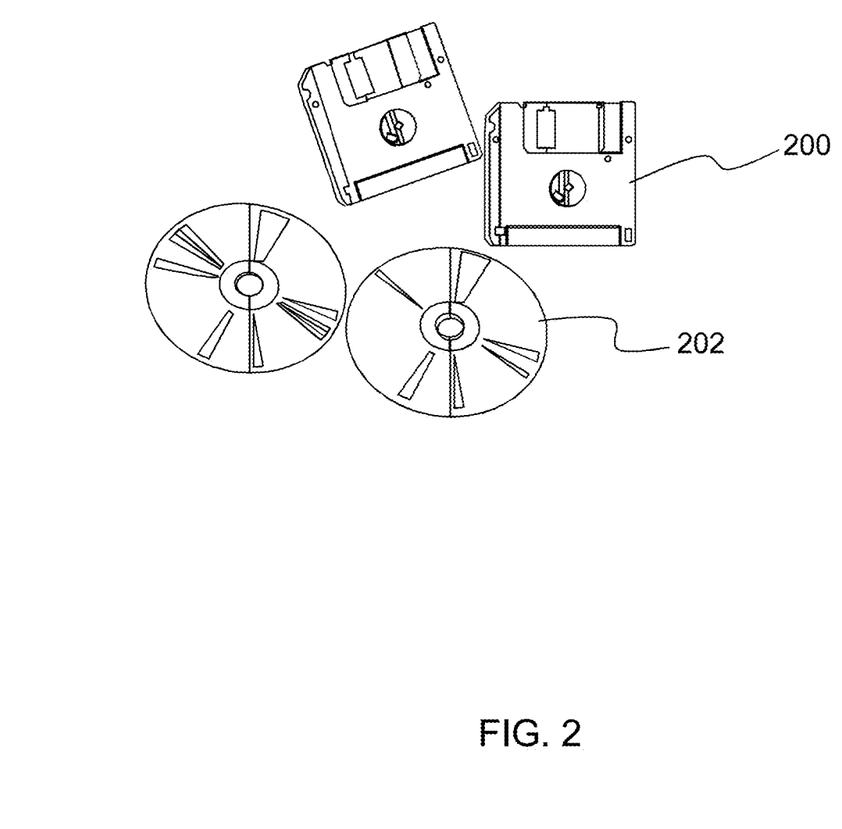
FIG. 2 is an illustration of a computer program product according to some embodiments of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) SPECIFIC DETAILS OF VARIOUS EMBODIMENTS

Described is an improved brain-machine interface (BMI), which enhances the efficacy of current brain-machine interfaces. Particularly, the improved BMI according to embodiments of the present disclosure addresses the challenges of: 1) learning to control devices controlled by neural activity, and 2) maintaining effective neural control of devices over extended use. The system is comprised of a portable system that integrates neural signal measurements (e.g., electroencephalogram, functional near infrared spectroscopy, etc.) and a transcranial stimulator (i.e., alternating current, direct current, focused ultrasound, photoacoustics) for use during constrained or unconstrained scenarios, and in open- or closed-loop configuration. Note that a transcranial stimulator can also apply sensory stimuli, such as auditory or visual cues. The closed-loop operation determines the transcranial stimulator parameters (e.g., phase, frequency) based on ongoing brain states (e.g., slow-wave oscillations in scalp electroencephalogram during sleep), as opposed to open-loop operation, which does not rely on feedback from ongoing brain states.

Leveraging recent insights from sleep stimulation work and memory, neuromodulation can be applied through STAMP (spatiotemporal amplitude-modulated patterns) tagging of desired behavior during active periods and consolidation during sleep (as described in U.S. application Ser. No. 15/332,787, which is hereby incorporated by reference as though fully set forth herein), as well as through other neuromodulatory modalities, including auditory or visual cues. The invention described herein enables individuals utilizing neural interfaces to achieve a higher degree of freedom (DOF) output system control, to improve stability of the neural interface as a whole during extended duration use, and to decrease the amount of training time necessary to learn control modulation. The majority of systems that provide both sensing and control interfaces address limitations in control through the restriction of decoded output to a handful of reliable signals (see Literature Reference No. 1). Beyond the limitation of the throughput and control bits available, the prior technique is non-intuitive and time-consuming for users as they require extensive chaining of primitives to perform complex tasks or the use of more intuitive modalities, such as electromyography (EMG), that require leeching off another extremity (see Literature Reference No. 2).

Furthermore, extended duration use of any neural interface makes it less robust and requires repeated calibration to be performed throughout the day to ensure accurate and reliable function (see Literature Reference Nos. 3 and 4). While improvements in neural decoders are being made to address this issue as well as improving overall performance (see Literature References Nos. 5 and 6), calibration remains the most reliable solution in lieu of extensive amounts of subject-specific neural data.

Lastly, learning to control neural interfaces is difficult as it requires manipulating a process that normally operates invisibly and effortlessly day-to-day. Existing mitigation techniques rely on training individuals to induce increased neural activity indirectly by thinking about specific tasks or objects, or directly by actively engaging with a system, such as a videogame. While effective for a few control outputs, this becomes difficult to leverage for numerous control outputs and, consequently, generalizes poorly. By directly addressing key limitations in neural interfaces, the system according to embodiments of the present disclosure enables effective, high degree-of-freedom (DOF) utilization of neural interfaces in a host of applications ranging from prostheses to games.

The following is a description of the application of an individual utilizing the brain-machine interface described herein to control a prosthetic device, such as a robotic arm. This application is selected as an example due to the large number of control parameters required to fully articulate an upper body prosthetic. Moreover, due to the typical heavy use of the prostheses, this interface necessitates long-term stability of the decoders utilized.

Figure 3:
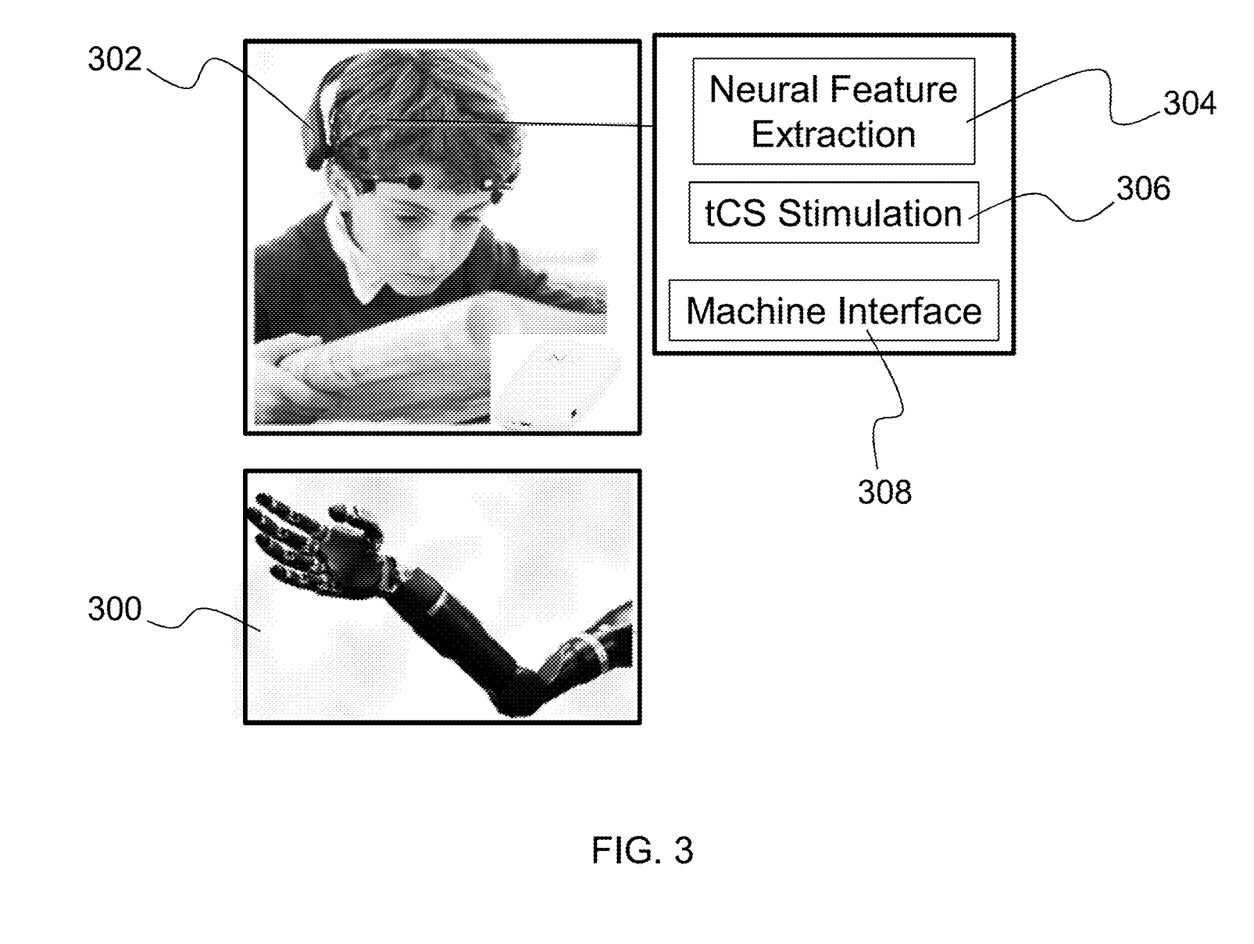
FIG. 3 is a diagram illustrating a system for neuromodulation in prosthetic control according to some embodiments of the present disclosure.

FIG. 3 depicts a non-limiting example of a system (e.g., portable device) implementing the invention described herein for controlling a prosthetic limb 300. The core system is composed of measurement, processing, and communication components. The measurements may be performed with electroencephalography (EEG) electrodes, or any other invasive or non-invasive neural recording technology, such as functional near infrared spectroscopy (fNIRS) and electrocorticography (ECoG). These sensors would be utilized in a portable headset 302 or other head-mounted platform, such as a neural headcap or headgear. For example, the portable headset 302 can be a headcap containing sensors to detect high-resolution spatiotemporal neurophysiological activity. The portable headset 302 can also include stimulation elements for directing current flow to specific neural regions. It should be understood that additional headgear configurations can also be implemented, such as a non-elastic headcap, nets (such as hair or head nets), bands, visors, helmets, or other headgear.

In one aspect, the neural interface and intervention system described herein comprises one or more electrodes or transducers (electrical, magnetic, optical, ultrasonic) in contact with the head, which is capable of sensing and/or applying stimulation. The one or more electrodes can be non-invasive (e.g., surface of head) or invasive (e.g., brain). The electrodes (or other neural sensors) measure differences in voltage between neurons in the brain. The signal is then processed (e.g., amplified, filtered) as described below, then automatically interpreted by a computer program to generate control commands for the machine (e.g., prosthetic limb).

In one embodiment, a portable device collects neural signals of interest as described above. The portable device could also take input from the environment through other sensors attached with the portable device (e.g., global positioning system (GPS) coordinates, accelerometer data, gyro sensor data) to mark behavioral or neural events of interest and determine the appropriate stimulation patterns. In another aspect, a portable device both collects and processes signals of interest as well as administers neuromodulation to the brain. In yet another embodiment, a portable device may collect and process signals, apply neuromodulation, and interface with a controllable system (such as a prosthetic arm or a remote robot). The collected signals are then, in real-time, processed by a portable processing component (either a dedicated device, or through the use of a mobile application) that conditions the neural data and performs neural feature extraction 304 to extract the salient neural features.

Furthermore, as novel decoders are created regularly, the processing component supports the integration of on-board or remote co-processing modules that assist in interpreting the neural output. Moreover, as noted above, the processing component also takes input to mark behavioral or neural events of interest and determine the appropriate stimulation patterns. The stimulation patterns, when electrical, will follow U.S. application Ser. No. 15/332,787. Briefly, the approach is composed of applying unique spatiotemporal amplitude-modulated patterns (STAMPs) of stimulation (e.g., transcranial current stimulation (tCS) 306) to tag and cue memories, applied via a suitable stimulation device to salient physiological regions depending on the task the user wishes to perform (e.g., controlling a prosthetic arm to reach for an object or to grasp and lift an object). The brain regions involved in the planning and execution of individual tasks, if known from the functional neuroimaging of the user's brain, can be accordingly targeted with STAMPs. Other neuromodulatory techniques can be applied as appropriate.

Figure 4:
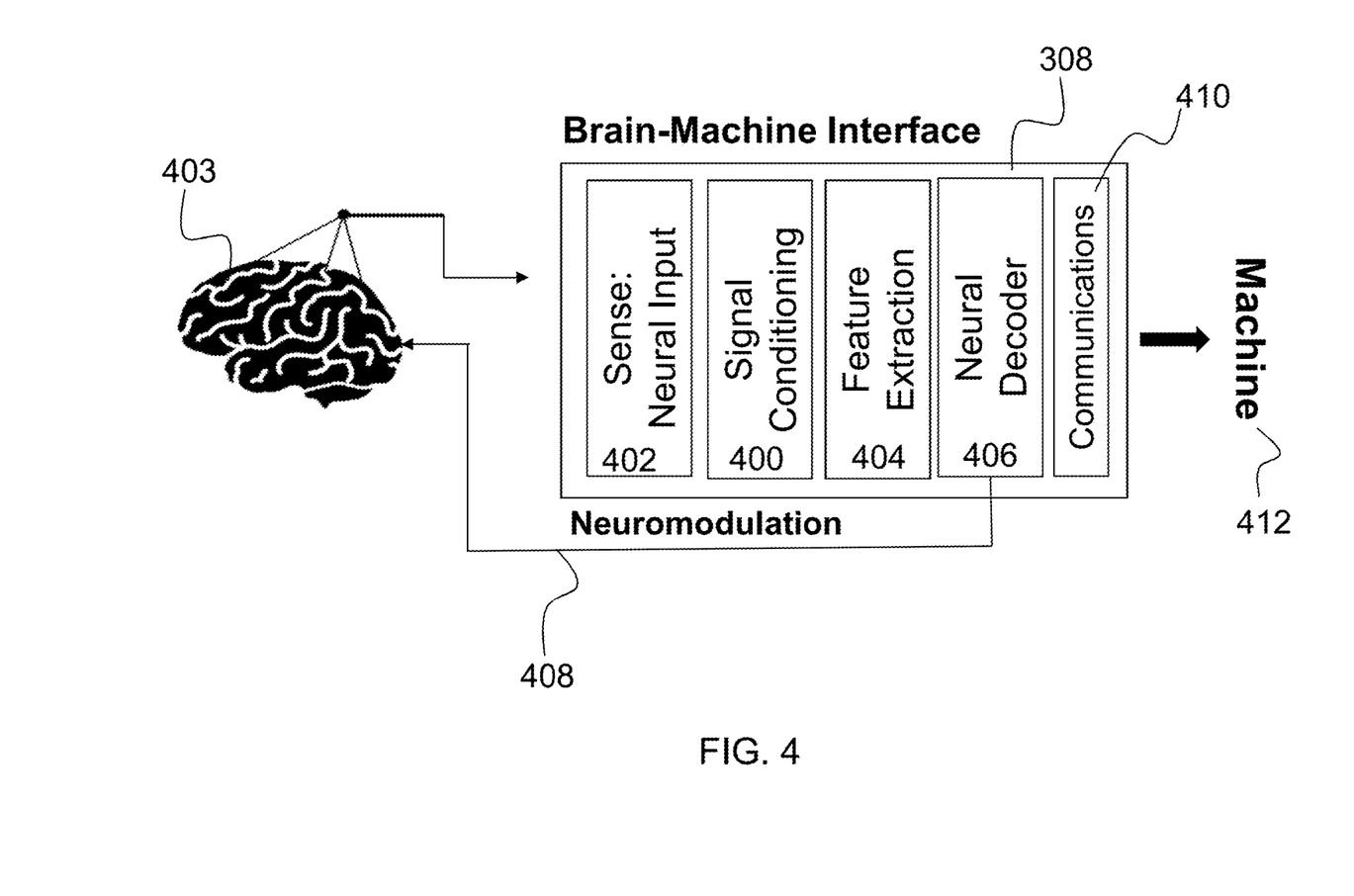
FIG. 4 is a diagram illustrating control of a brain-machine interface according to some embodiments of the present disclosure.

Lastly, the communication component provides the ability to manipulate external systems through the BMI 308. While the interface for the controllable device requires an application programming interface (API) or other analog/digital interface, the invention described herein provides a standard communication layer to access the trained and processed brain activity in the form of discrete or continuous control signals. A system diagram depicting the different components of the system according to embodiments of the present disclosure is shown in FIG. 4. The following is a detailed description of the subsystems and their implementation.

(3.1) Signal Conditioning 400

Upon receiving a neural input 402 from a brain 403 from, for instance, electrodes (EEG, ECoG, fNIRS), the signal conditioning component 400 of the invention provides the feature extraction component 404 and the neural decoder component 406 with a clean underlying signal. Utilizing recent research conducted at HRL Laboratories (see Literature Reference No. 8) as well as examining literature for best practices in conditioning, the following set of steps provides a sample implementation for signal conditioning.
1. Remove common channel noise if the measurement modality requires it. Situations where this may be required would be where noise is introduced into other channels due to poor wire harness isolation, or there is a common external noise generator present in all channels.
2. Correct signal drift. This process involves removing the linear trend from the signal vector to ensure an average signal slope of ~0.
3. Where necessary, create virtual channels to provide better spatial representation of neural activation in the feature space. Alternatively, independent component analysis (ICA) can be utilized to extract the signal components from the shared (noisy) neural recording space to provide a source-centric signal for use in the feature extraction component 404.

(3.2) Feature Extraction 404

The feature extraction component 404 of the system diagram (FIG. 4) provides the neural decoder component 406 with signal components that are a rich summary of the neural temporal signals. This can include anything from signal power in physiological ranges of interest (e.g., stereotypical delta, alpha, beta, theta, gamma, and/or high-gamma ranges) to unsupervised features extracted using autoencoders. EEG is a representative source of signals. An autoencoder is a neural network that can be trained to learn a compressed representation of the inputs. A subject expert is used to identify the features of interest and provide the algorithms to extract them for use down-stream. For example, a subject expert may suggest beta-power and signal coherence be utilized for gross motor movement, or high-gamma power for higher-order cognitive decoding, and even using beta-high-gamma- and signal coherence for speech decoding.

(3.3) Neural Decoder 406

The neural decoder component 406 is the second-to-last step in the brain-machine interface 308; it provides a learned mapping between the input neural feature space and the output application control space. While any state-of-the-art algorithm may be utilized for providing this learned projection (i.e., Conv-LSTMs (convolutional long short-term memories), RNNs (recurrent neural networks), and linear models such as LDA (Linear Discriminant Analysis)), the innovation stems from the neuromodulation stimulation 408.

In a typical use case, a prior art neural decoder component is trained on a set of data and then requires recalibration when signal dynamics or quality change. In contrast, the neuromodulation stimulation 408 according to embodiments of the present disclosure provides reinforcement to the user via stimulation (e.g., electrical, auditory, visual) during training and during normal use to ensure neural decoder 406 stability and enhanced accuracy. The stability, in particular, is induced by the reinforcement of particular neural dynamics via external innervation. The neural decoder 406 accuracy, consequently, is exhibited via the stereotypical neuronal activation pathway resulting from the stimulation reinforcement (i.e., neuromodulation stimulation 408). While stimulation during training would follow a strict regimen to ensure rapid adaptation to the controller, the testing reinforcement would occur during high-confidence decoding intervals where a fluctuation in signal characteristics are observed prior (i.e., signal-to-noise changes, signal dynamics changes).

(3.3.1) Neurostimulation/Neuromodulatory Feedback

While the modality of the neurostimulatory/neuromodulatory feedback via neuromodulation stimulation 408 can be one of many choices, including electrical, auditory, and optical, the STAMP technique can also be utilized. In particular, the initial training setup (during waking) would be composed of a closed-loop performance monitoring system that would measure the user's performance on a desired task and apply STAMP stimulation to tag behavioral events. During sleep, the brain activity patterns underlying desired behaviors (e.g., correct operation or movement of the prosthetic arm in a particular trial) can be reactivated using the application of relevant STAMPs to promote long-term stability and consolidation. Depending on the task, the stimulation may be focal to brain regions of interest (e.g., sensorimotor cortex) or region-indiscriminate stimulation for more complex behaviors. Once a baseline performance that is acceptable to the user is achieved, the dedicated training process is complete.

During normal use, the user or a teacher will manually tag behaviors that are desirable by applying unique STAMPs from start to finish of behavioral sequences. Upon sleeping, the user would receive simulation that would again reinforce the desired behaviors with respect to the controllable device (e.g., prosthetic arm). Furthermore, in high-cognitive load environments, the system would be able to provide preemptive stimulation in real-time to reinforce the neural dynamics for a particular behavior decreasing the pathway threshold for a desired behavior to be exhibited. This type of use would support controller use in conditions where mental fatigue is adversely affecting the decoder performance.

As described above, the invention described herein provides the ability to manipulate external systems through the brain-machine interface 308. The standard communication layer 410 transmits the decoded parameters from the processed brain activity in the form of discrete or continuous control signals for operating the different actuators of the controllable device (e.g., joints of a prosthetic arm). The communication layer 410 controls output from the neural interface (wireless or wired, and digital or analog) that is supplied to the machine that the individual is controlling.

As described above, a unique aspect of the invention described herein is the use of the neuromodulation stimulation 408 to tag desirable behaviors during waking and cue them during sleep as reinforcement for them to be seamlessly used in controlling external devices/machines 412 (e.g., prosthetic limb, remote robot), as well as improving the robustness of such a system by enhancing the neural repeatability of signals involved with conditioning. Multiple usage scenarios exist for the system according to embodiments of the present disclosure, but two primary techniques are described: classical train-test and online train-test. The classical approach is what is typically used to train neural interfaces. A user performs the desired task numerous times and the neural data is used to train a decoder offline. Once enough data is collected for the desired behavior and the neural decoder is capable of achieving some performance, the user may use the interface (typically for a few hours) before requiring recalibration. Applying the invention described herein to this approach, an automated or manual approach for tagging desirable behaviors during training is performed and the stimulation is applied accordingly.

The online train-test approach is more flexible in its expandability of control primitives with the caveat of requiring user intervention during use. In this approach, a user is trained classically on a set of base primitives. During regular use, however, the user can add more neural responses for use in the control dictionary. The user would simply use one of the base primitives already trained, or using a physical input such as a button force the system to use the last few instances in time as favorable behavior for a new or reinforced control signal. This approach allows for more gradual learning as opposed to the learning of all control signals at once in the classical technique described above.

Both the classical and online techniques for learning the control primitives can be applied in an open-loop and closed-loop manner. The open-loop approach simply does not allow the user to retrain the model once the models are trained to achieve a certain performance. The closed-loop approach allows for stimulation to occur to condition the neural response during regular use and can better control the neural dynamics robustness over time.

The closest existing prior art that addresses the enhancement of brain-machine interfaces was performed by Pan et al. (see Literature Reference No. 7) and focused on using transcranial direct current stimulation to improve the electromyographic response of the peripheral muscles rather than the central nervous system. This is a sharp contrast to the system described herein in that the system utilizes stimulation to improve the neurophysiological response in the brain (i.e., the central nervous system), not the peripheral muscles, and then utilizes that signal to directly control a machine. Beyond neuromodulation, other techniques for improving brain-machine interfaces have focused on the improvement of sensor readings and improving decoding techniques. While these improvements are important, the present invention can utilize not only these advances, but also provide more conditioned neural responses to these sensors and decoders by manipulating the underlying neural dynamics. No comparable techniques exist for improving brain-machine interfaces through the use of neuromodulation. All prior approaches that utilize neuromodulation focus on utilizing it for improvement of cognitive tasks or physical therapy. The primary reason for this is the limited amount of research in the field; as such, the invention described herein leverages recent advances that allow this technique to be utilized effectively. Other prior approaches to improving brain-machine interfaces have been sensor and decoder-centric. As sensors improve the performance of all neural interfaces, they are an orthogonal comparison; however, the decoder improvements address some of the challenges addressed by the present invention. However, in addressing accuracy of the neural interface, more advanced decoders that perform well over an extended duration without retraining or recalibration to the subject require a significant amount of data. As such, the invention provides an approach that not only addresses the challenges of existing brain-machine interfaces, but also retains the advantages afforded by other advances in neural interface work.

While numerous applications exist in the medical, commercial, and defense spaces, a potential application is medicine with a focus on prosthetic control (i.e., supporting the recovery of veterans who have lost limbs). Other applications include controlling an exoskeleton for able-bodied individuals to perform super-human tasks, and a remote robot performing search-and-rescue operations in dangerous circumstances.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. An enhanced brain-machine interface with neuromodulation, the enhanced brain-machine interface comprising:
    a neural interface and a controllable device in communication with the neural interface,
    wherein the neural interface comprises:
        a neural device having one or more sensors for collecting signals of interest, wherein the neural device is configured to administer a neuromodulation stimulation; and
        one or more processors and a non-transitory computer-readable medium having executable instructions encoded thereon such that when executed, the one or more processors perform an operation of:
            conditioning the signals of interest, resulting in conditioned signals of interest;
            extracting salient neural features from the conditioned signals of interest;
            decoding the salient neural features, providing a mapping between an input neural feature space and an output control space for the controllable device;
            based on the mapping, generating at least one control command for the controllable device;
            causing the controllable device to perform one or more operations according to the at least one control command; and
            causing the neural device to administer the neuromodulation stimulation to reinforce operation of the controllable device, wherein the neuromodulation stimulation comprises unique spatiotemporal amplitude-modulated patterns (STAMPs) of stimulation.

2. The system as set forth in claim 1, wherein the signals of interest comprise at least one of neural signals and environmental signals.

3. The system as set forth in claim 1, wherein the neuromodulation stimulation is one of auditory, visual, and electrical stimulation.

4. The system as set forth in claim 1, wherein the controllable device is a prosthetic limb.

5. The system as set forth in claim 1, wherein the one or more neural sensors comprises one or more electrodes configured to perform at least one of sensing and applying stimulation.

6. A method for implementing an enhanced brain-machine interface with neuromodulation, the method comprising an act of:
causing one or more processers to execute instructions encoded on a non-transitory computer-readable medium, such that upon execution, the one or more processors perform operations of:
conditioning signals of interest obtained from a neural device having one or more sensors, wherein the neural device is configured to administer a neuromodulation stimulation;
extracting salient neural features from the conditioned signals of interest;
decoding the salient neural features, providing a mapping between an input neural feature space and an output control space for the controllable device;
based on the mapping, generating at least one control command for the controllable device;
causing the controllable device to perform one or more operations according to the at least one control command; and
causing the neural device to administer the neuromodulation stimulation to reinforce operation of the controllable device, wherein the neuromodulation stimulation comprises unique spatiotemporal amplitude-modulated patterns (STAMPs) of stimulation.

7. The method as set forth in claim 6, wherein the signals of interest comprise at least one of neural signals and environmental signals.

8. The method as set forth in claim 6, wherein the neuromodulation stimulation is one of auditory, visual, and electrical stimulation.

9. The method as set forth in claim 6, wherein the controllable device is a prosthetic limb.

10. The method as set forth in claim 6, wherein the one or more neural sensors comprises one or more electrodes configured to perform at least one of sensing and applying stimulation.

11. A computer program product for implementing an enhanced brain-machine interface with neuromodulation, the computer program product comprising:
computer-readable instructions stored on a non-transitory computer-readable medium that are executable by a computer having one or more processors for causing the processor to perform operations of:
conditioning signals of interest obtained from a neural device having one or more sensors, wherein the neural device is configured to administer a neuromodulation stimulation;
extracting salient neural features from the conditioned signals of interest;
decoding the salient neural features, providing a mapping between an input neural feature space and an output control space for the controllable device;
based on the mapping, generating at least one control command for the controllable device;
causing the controllable device to perform one or more operations according to the at least one control command; and
causing the neural device to administer the neuromodulation stimulation to reinforce operation of the controllable device, wherein the neuromodulation stimulation comprises unique spatiotemporal amplitude-modulated patterns (STAMPs) of stimulation.

12. The computer program product as set forth in claim 11, wherein the signals of interest comprise at least one of neural signals and environmental signals.

13. The computer program product as set forth in claim 11, wherein the neuromodulation stimulation is one of auditory, visual, and electrical stimulation.

14. The computer program product as set forth in claim 11, wherein the controllable device is a prosthetic limb.

15. The computer program product as set forth in claim 11, wherein the one or more neural sensors comprises one or more electrodes configured to perform at least one of sensing and applying stimulation.

* * * * *